(12) United States Patent
Wirch et al.

(10) Patent No.: US 11,231,575 B2
(45) Date of Patent: *Jan. 25, 2022

(54) VIRTUAL SLIDE STAGE (VSS) METHOD FOR VIEWING WHOLE SLIDE IMAGES

(71) Applicant: Corista, LLC, Concord, MA (US)

(72) Inventors: Eric W. Wirch, Somerville, MA (US); David C. Wilbur, Pelham, NH (US); Richard Y. Wingard, II, Newton, MA (US); Michael Ryan Tomer, Auburn, ME (US); Kevin Christopher Dorosh, North Reading, MA (US); Jonathan Mitchell Gaines, Seabrook, TX (US); Odell Christian Dotson, Medford, MA (US); Aristana Olivia Scourtas, Nahant, MA (US)

(73) Assignee: CORISTA, LLC, Concord, MA (US)

( * ) Notice: Subject to any disclaimer, the term of this patent is extended or adjusted under 35 U.S.C. 154(b) by 66 days.

This patent is subject to a terminal disclaimer.

(21) Appl. No.: 16/849,766

(22) Filed: Apr. 15, 2020

(65) Prior Publication Data
US 2020/0348503 A1    Nov. 5, 2020

Related U.S. Application Data

(63) Continuation of application No. 15/730,296, filed on Oct. 11, 2017, now Pat. No. 10,663,711.

(Continued)

(51) Int. Cl.
*G02B 21/36* (2006.01)
*G02B 21/34* (2006.01)
(Continued)

(52) U.S. Cl.
CPC .......... *G02B 21/365* (2013.01); *G02B 21/26* (2013.01); *G02B 21/34* (2013.01); *G06K 9/00127* (2013.01); *G16H 30/20* (2018.01)

(58) Field of Classification Search
None
See application file for complete search history.

(56) References Cited

U.S. PATENT DOCUMENTS

| 5,561,556 A | 10/1996 | Weissman |
| 5,733,721 A | 3/1998 | Hemstreet, III et al. |

(Continued)

FOREIGN PATENT DOCUMENTS

| WO | 2017/087415 A1 | 5/2017 |
| WO | 2018/129318 A2 | 7/2018 |
| WO | 2019226270 A8 | 11/2019 |

OTHER PUBLICATIONS

Notification of Transmittal of the International Search Report and Written Opinion of the International Searching Authority from counterpart International Application No. PCT/US2018/012584, "Virtual Slide Stage (VSS) Method for Viewing Whole Slide Images," dated Jul. 6, 2018.

(Continued)

*Primary Examiner* — Michelle M Entezari
(74) *Attorney, Agent, or Firm* — Hamilton, Brook, Smith & Reynolds, P.C.

(57) ABSTRACT

Embodiments provide slide navigation technology that addresses challenges in digital pathology of navigating and viewing high resolution slide images. Example systems comprise a virtual slide stage (VSS) having at least one sensor that detects user movement of a target placed on the VSS, and an input component, coupled to the VSS, which provides quick function movement control of the target via quick functions. The systems also comprise a connector component that connects the VSS to a user device and transmits output from the at least one sensor and input component to the user device. The systems further comprise a computer processor, in communication with the VSS, which processes the output using a computational model to (Continued)

generate data representing movement profiles of the target. The computer processor executes a software component, causing the output, translated based on the movement profiles, to be relayed via a viewing application on the user device.

18 Claims, 5 Drawing Sheets

Related U.S. Application Data

(60) Provisional application No. 62/442,403, filed on Jan. 4, 2017.

(51) Int. Cl.
   *G02B 21/26* (2006.01)
   *G06K 9/00* (2006.01)
   *G16H 30/20* (2018.01)

(56) References Cited

U.S. PATENT DOCUMENTS

| | | | |
|---|---|---|---|
| 5,741,648 A | 4/1998 | Hemstreet, III et al. | |
| 5,956,418 A | 9/1999 | Alger et al. | |
| 6,011,809 A | 1/2000 | Tosaka | |
| 6,049,421 A | 4/2000 | Raz et al. | |
| 6,466,352 B1 | 10/2002 | Shahar et al. | |
| 6,606,413 B1 | 8/2003 | Zeineh | |
| 6,650,357 B1 | 11/2003 | Richardson | |
| 6,798,571 B2 | 9/2004 | Wetsel et al. | |
| 6,905,300 B1 | 6/2005 | Russum | |
| 6,961,080 B2 | 11/2005 | Richardson | |
| 7,109,464 B2 | 9/2006 | Cartlidge | |
| 7,132,636 B1 | 11/2006 | Cartlidge et al. | |
| 7,151,246 B2 | 12/2006 | Fein et al. | |
| 7,155,049 B2 | 12/2006 | Wetzel et al. | |
| 7,224,839 B2 | 5/2007 | Zeineh | |
| 7,248,716 B2 | 7/2007 | Fein et al. | |
| 7,338,168 B2 | 3/2008 | Cartlidge et al. | |
| 7,346,200 B1 | 3/2008 | Tsipouras et al. | |
| 7,417,213 B2 | 8/2008 | Krief | |
| 7,463,761 B2 | 12/2008 | Eichhorn et al. | |
| 7,518,652 B2 | 4/2009 | Olson et al. | |
| 7,522,757 B2 | 4/2009 | Tsipouras et al. | |
| 7,605,356 B2 | 10/2009 | Krief et al. | |
| 7,638,748 B2 | 12/2009 | Krief et al. | |
| 7,640,112 B2 | 12/2009 | Tsipouras et al. | |
| 7,646,495 B2 | 1/2010 | Olsen et al. | |
| 7,689,024 B2 | 3/2010 | Eichhorn et al. | |
| 7,692,131 B2 | 4/2010 | Fein et al. | |
| 7,756,357 B2 | 7/2010 | Yoneyama | |
| 7,772,535 B2 | 8/2010 | Krief et al. | |
| 7,835,869 B2 | 11/2010 | Tsipouras et al. | |
| 7,863,552 B2 | 1/2011 | Cartlidge et al. | |
| 7,867,126 B2 | 1/2011 | Nakajima et al. | |
| 7,876,948 B2 | 1/2011 | Wetzel et al. | |
| 7,901,887 B2 | 3/2011 | Tafas et al. | |
| 7,945,391 B2 | 5/2011 | Tsipouras et al. | |
| 8,170,698 B1 | 5/2012 | Gusack | |
| 8,271,251 B2 | 9/2012 | Schwartz et al. | |
| 8,574,590 B2 | 11/2013 | Doranz et al. | |
| 8,774,518 B2 | 7/2014 | Cosatto et al. | |
| 8,879,813 B1 | 11/2014 | Solanki et al. | |
| 8,891,851 B2 | 11/2014 | Spaulding | |
| 8,896,620 B2 | 11/2014 | Orrock | |
| 8,897,537 B2 | 11/2014 | Cosatto et al. | |
| 8,934,699 B2 | 1/2015 | Yamane et al. | |
| 8,934,718 B2 | 1/2015 | Cosatto et al. | |
| 9,036,255 B2 | 5/2015 | Loney et al. | |
| 9,097,909 B2 | 8/2015 | Halushka | |
| 9,134,524 B2 | 9/2015 | Yamamoto et al. | |
| 9,213,027 B2 | 12/2015 | Doranz et al. | |
| 9,217,694 B2 | 12/2015 | Sieckmann et al. | |
| 9,224,106 B2 | 12/2015 | Cosatto et al. | |
| 9,332,190 B2 | 5/2016 | Murakami | |
| 9,335,534 B2 | 5/2016 | Schlaudraff | |
| 9,430,829 B2 | 8/2016 | Madabhushi et al. | |
| 9,547,898 B2 | 1/2017 | Hall et al. | |
| 9,575,301 B2 | 2/2017 | Loney et al. | |
| 9,581,800 B2 | 2/2017 | Corwin et al. | |
| 9,609,196 B2 | 3/2017 | Yamakawa et al. | |
| 9,712,732 B2 | 7/2017 | Kaneko et al. | |
| 9,759,551 B2 | 9/2017 | Schlaudraff et al. | |
| 9,772,282 B2 | 9/2017 | Tucker-Schwartz et al. | |
| 9,791,659 B2 | 10/2017 | Yamakawa | |
| 9,805,166 B1 | 10/2017 | Spaulding | |
| 9,818,190 B2 | 11/2017 | Chukka et al. | |
| 9,846,938 B2 | 12/2017 | Steigauf et al. | |
| 9,892,341 B2 | 2/2018 | Reicher et al. | |
| 9,928,278 B2 | 3/2018 | Welinder et al. | |
| 9,934,568 B2 | 4/2018 | Reicher et al. | |
| 9,940,719 B2 | 4/2018 | Kneepkens | |
| 9,963,745 B2 | 5/2018 | Mai et al. | |
| 9,972,087 B2 | 5/2018 | Isoda et al. | |
| 9,977,230 B2* | 5/2018 | Yuri | G06T 5/50 |
| 9,979,868 B2 | 5/2018 | Fujinami et al. | |
| 10,012,537 B2 | 7/2018 | Garsha et al. | |
| 10,048,462 B2 | 8/2018 | Mitsuyasu | |
| 10,049,450 B2 | 8/2018 | Madabhushi et al. | |
| 10,061,107 B2 | 8/2018 | Loney et al. | |
| 10,102,418 B2 | 10/2018 | Bredno et al. | |
| 10,175,154 B2 | 1/2019 | Campbell | |
| 10,185,804 B2* | 1/2019 | Yoshioka | G16H 30/20 |
| 10,201,330 B2* | 2/2019 | Nielsen | G06F 3/04886 |
| 10,444,486 B2 | 10/2019 | Rainbolt et al. | |
| 10,489,633 B2 | 11/2019 | Molin et al. | |
| 10,527,836 B2 | 1/2020 | Sakamoto et al. | |
| 10,572,725 B1 | 2/2020 | Becker et al. | |
| 10,573,001 B2 | 2/2020 | Bredno et al. | |
| 10,600,184 B2 | 3/2020 | Golden et al. | |
| 10,643,396 B2 | 5/2020 | Eastwood et al. | |
| 10,663,711 B2 | 5/2020 | Wirch et al. | |
| 10,943,346 B2 | 3/2021 | Wirch et al. | |
| 2008/0123916 A1 | 5/2008 | Adams et al. | |
| 2010/0194681 A1 | 8/2010 | Halushka | |
| 2011/0158491 A1 | 6/2011 | Markova et al. | |
| 2011/0221881 A1* | 9/2011 | Shirota | G02B 21/367 348/79 |
| 2012/0002034 A1 | 1/2012 | Matsunobu et al. | |
| 2012/0068928 A1 | 3/2012 | Bruss et al. | |
| 2013/0077891 A1 | 3/2013 | Nimnual et al. | |
| 2013/0339260 A1 | 12/2013 | Johnson | |
| 2014/0098213 A1* | 4/2014 | Sato | G02B 21/367 348/79 |
| 2014/0257857 A1 | 9/2014 | Meissner et al. | |
| 2014/0368633 A1* | 12/2014 | Le Naour | G02B 27/026 348/80 |
| 2015/0110348 A1 | 4/2015 | Solanki et al. | |
| 2015/0279032 A1 | 10/2015 | Hall et al. | |
| 2015/0330776 A1 | 11/2015 | Hayashi et al. | |
| 2016/0019691 A1 | 1/2016 | Imamura et al. | |
| 2016/0019695 A1 | 1/2016 | Chukka et al. | |
| 2016/0042511 A1 | 2/2016 | Chukka et al. | |
| 2016/0157751 A1 | 6/2016 | Mahfouz | |
| 2016/0252713 A1 | 9/2016 | Corwin | |
| 2016/0321809 A1 | 11/2016 | Chukka et al. | |
| 2016/0350651 A1 | 12/2016 | Devarajan et al. | |
| 2017/0169567 A1 | 6/2017 | Chefd'hotel et al. | |
| 2017/0185846 A1 | 6/2017 | Hwangbo et al. | |
| 2017/0348509 A1 | 12/2017 | Burkholz et al. | |
| 2017/0372471 A1 | 12/2017 | Euren | |
| 2018/0188519 A1 | 7/2018 | Wirch et al. | |
| 2018/0247408 A1 | 8/2018 | Wang et al. | |
| 2018/0315193 A1 | 11/2018 | Paschalakis et al. | |
| 2018/0322632 A1 | 11/2018 | Barnes et al. | |
| 2018/0374210 A1 | 12/2018 | Barker et al. | |
| 2019/0164054 A1 | 5/2019 | Lee et al. | |
| 2019/0293637 A1 | 9/2019 | Day et al. | |
| 2019/0304092 A1 | 10/2019 | Akselrod-Ballin et al. | |
| 2019/0355113 A1 | 11/2019 | Wirch et al. | |
| 2019/0362841 A1 | 11/2019 | Aysin et al. | |
| 2020/0126207 A1 | 4/2020 | Saltz et al. | |

(56) References Cited

U.S. PATENT DOCUMENTS

2020/0167930 A1    5/2020  Wang et al.
2020/0211191 A1    7/2020  Joshi
2020/0264096 A1*   8/2020  Boamfa ............. G02B 21/0076

OTHER PUBLICATIONS

Rojo, M.G., et al., "Critical Comparison of 31 Commercially Available Digital Slide Systems in Pathology," International Journal of Surgical Pathology, vol. 14, No. 4, pp. 285-305, Oct. 1, 2006.
International Preliminary Report on Patentability for International Application No. PCT/US2018/012584, titled: Virtual Slide Stage (VSS) Method for Viewing Whole Slide Images, dated Jul. 9, 2019.
Trahearn, Nicholas et al., "Hyper-Stain Inspector: A Framework for Robust Registration and Localised Co-Expression Analysis of Multiple Whole-Slide Images of Serial Histology Sections," Scientific Reports, 7: 5641, 13 pages (published Jul. 2017).
Roullier, Vincent et al., "Multi-resolution graph-based analysis of histopathological whole slide images: Application to mitotic cell extraction and visualization," Computerized Medical Imaging and Graphics, 35: 603-615 (2011).
Notice of Allowance and Fees Due for U.S. Appl. No. 15/730,296, entitled "Virtual Slide Stage (VSS) Method For Viewing Whole Slide Images," dated Mar. 11, 2020.

\* cited by examiner

VIRTUAL SLIDE STAGE (VSS) METHOD FOR VIEWING WHOLE SLIDE IMAGES

RELATED APPLICATIONS

This application is a continuation of U.S. application Ser. No. 15/730,296, filed Oct. 11, 2017, which claims the benefit of U.S. Provisional Application No. 62/442,403, filed on Jan. 4, 2017. The entire teachings of the above applications are incorporated herein by reference.

FIELD OF INVENTION

The present invention is directed to a system, method, and apparatus for navigation of virtual images.

BACKGROUND

Navigation of very high resolution Whole Slide Images (WSIs) in digital pathology is challenging when attempted over extended sessions or time periods. The frequency and scale of mouse movements needed, the unfamiliarity of keyboard controls for navigating, and the gross-scale arm movements needed to use a touch screen with a sufficient resolution for a diagnostically relevant image are all barriers toward effective WSI navigation.

In contrast, reviewing slides using a microscope is a quick process, requiring very fine finger movements to scan a slide at an overview level, then rapidly realigning and jumping to significantly higher magnifications. Microscope stages have fine controls for moving the slide in the horizontal and vertical (X & Y) directions, but many pathologists do not even use these controls, instead opting to manipulate the slide directly with their fingertips.

SUMMARY

Embodiments of the present invention are directed to a Virtual Slide Stage (VSS) method and system, which provide a solution that allows for a pathologist to effectively review a complete set of digital Whole Slide Images (WSIs) for a given case. This review of WSIs occurs in the place of a review of the corresponding physical slides. The usability and ergonomics of the VSS closely emulate the process by which a user reviews a set of physical slides with a microscope. The VSS facilitates the user virtually reviewing WSIs for the given case by: (a) enabling switching from one slide to the next via a quick function, (b) enabling navigation within a slide via fine motor movements (physically similar to the movements that pathologists are accustomed to using for reviewing physical slides), (c) quickly changing magnifications via a quick function, (d) flagging key slides for later reference via a quick function, and (e) navigating between focal planes (Z-stacks) on images with multiple captured focal planes. This virtual review facilitated by the VSS has direct correlation to the steps in a physical review of slides, which include: (a) placing one of a series of slides on the stage, (b) navigating within a slide by physically moving the slide, (c) changing magnifications by switching objectives with the microscope turret, (d) flagging key slides with a permanent marker, and (e) adjusting the focal plane by adjusting the distance between an objective and the target.

Embodiments of the present invention provide slide navigation systems, methods, and devices that address challenges in digital pathology of navigating very high resolution slide images. These systems, methods, and devices enable virtually navigating and viewing Whole Slide Images (WSI), such that a pathologist may review a set of slides without physically handling them, utilizing skills analogous to physically reviewing slides. The systems include a virtual slide stage (VSS) having at least one sensor detecting user movement of a target placed on the VSS. The systems also include an input component, coupled to the VSS, which provides additional application movement control of the target via quick functions. The systems further include a connector component connecting the VSS to a user device. The connector component is configured to transmit output from the at least one sensor and the input component to the user device. The systems also include a computer processor, in communication with the VSS, which computationally processes the detected movement of the target relative to the VSS (transmitted output) using a computational model (movement profile) to generate processed movement data representing the desired movement of a WSI image in the viewing application. The computer processor executes a software component, which causes the generated processed movement data to be relayed via the viewing application executing on the user device.

In some embodiments of the systems, the VSS is further configured with a surface on which the target rests, and either: (i) the at least one sensor is configured within the surface, or (ii) a camera is mounted to the surface. In these embodiments of the systems, the at least one sensor of the VSS possesses sensitivity levels that enable detecting changes in position of the target relative to the VSS, including detecting slight changes in the position. In these embodiments of the systems, the computer processor may process the change in horizontal and vertical position of the target relative to the surface of the VSS, and may further process rotation of the target relative to the surface of the VSS.

In some embodiments of the systems, the VSS is further coupled to an artificial light source, the target is an opaque slide, and the at least one sensor includes at least one optical sensor that detect movement of the opaque slide by sensing light from the artificial light source. In some embodiments of the systems, the target is a translucent slide, and the at least one sensor includes at least one optical sensor that detects movement of the translucent slide by sensing ambient light. In some embodiments of the systems, the target is a blank slide, and the at least one sensor includes at least one infrared distance sensor that detects movement of the blank slide by sensing physical positioning of the blank slide.

In some embodiments of the systems, the target is an opaque slide, and the at least one sensor detects movement of the opaque slide via a camera, wherein at least one of coloration and marking are applied to facilitate the camera tracking and distinguishing the opaque slide from the VSS. In these embodiments of the systems, the camera may capture a new image of the target, and the computer processor calculates the movement of the target by comparing the captured new image to reference data stored in computer memory communicatively coupled to the computer processor. In some embodiments of the systems, the target is magnetized, and the at least one sensor further includes a set of magnetometers positioned below surface of the VSS. The set of magnetometers detect orientation and position of the magnetized target. In some embodiments of the systems, the at least one sensor detects movement of a touchscreen or touchpad, rather than the target.

In some embodiments of the systems, the quick functions may enable one or more keys or buttons coupled to the input component that is mounted or otherwise connected to the VSS, the one or more keys or buttons being at least one of physically-enabled or digitally-enabled components. In some embodiments of the systems, the quick functions may enable a dial or potentiometer, and accept at least one of: (i) digital inputs that enable one or more fixed settings and (ii) analog inputs that enable scrolling between discrete settings. In some embodiments of the systems, the quick functions may enable at least one of: gestures, camera detection, touchscreen, or touchpad. In some embodiments of the systems, the quick functions are in communication with the user device. In each of these embodiments, the quick functions enable: (i) switching between slides using the quick functions, (ii) navigating within a slide via fine motor movements, (iii) changing magnifications or resolutions using the quick functions, (iv) flagging key slides using the quick functions, and (v) switching between focal planes that have been captured and stored in the WSI.

In some embodiments of the systems, the connector component couples the VSS to the user device via at least one of: a USB connection, a wired-network, a WiFi network, and Bluetooth. In some embodiments of the systems, the processing of the detected movement is performed by the computer processor positioned either: (i) within the VSS or (ii) within the user device. In some embodiments of the systems, the processing is performed by the connected computer's processor (e.g., within the user device). In other embodiments, the processing is performed by a processor contained within the VSS. The processing transforms the detected data from the sensors and quick functions according to a user or system configuration that implements a movement profile, a model of movement of the VSS with respect to the movement of the target. The movement profile may be implemented to (i) remain linear to the movement of the target independent of magnification, (ii) geometrically scale to increase or decrease the responsiveness of the viewing application relative to the movement, or (iii) be user-configured, non-linear, and non-geometric. Once transformed, the movement and quick function data is transferred to the viewing application via at least one of (i) a native software or library, including a device driver, and (ii) a networking component, including a web server or websockets.

The methods of these embodiments detect, by at least one sensor coupled to a virtual slide stage (VSS), user movement of a target placed on the VSS. The methods further receive movement of the target by the user via quick functions, and transmit output from the at least one sensor and quick functions to the user device. The methods process the output using a model to generate processed movement data representing movement profiles of the target, and relay the output, translated based on the movement profiles, via a viewing application configured on the user device.

The devices of these embodiments include a virtual slide stage (VSS) having at least one sensor detecting user movement of a target placed on the VSS. The devices further include an input, coupled to the VSS, which provides quick function movement control of the target via quick functions. The devices further include a communication connection which connects the VSS to a user device and transmits output from the at least one sensor and the input component to the user device. The devices also include a computer processor, in communication with the VSS, which computationally processes the transmitted VSS output using a computational model to generate processed movement data representing movement profiles of the target. The computer processor executes software, which causes the transmitted VSS output translated based on the movement profiles, to be relayed via a viewing software application executing on the user device.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

The virtual slide stage (VSS) system and method of the present invention provides the primary purpose of quickly and efficiently viewing and navigating one or more Whole Slide Images (WSIs), representing a pathology case. Since WSIs are digital representations of physical slides, the viewing location is independent of the slide location.

A VSS system/device includes several basic components. The VSS system includes one or more sensors that detect the user's motion/movement of a target. The VSS system further includes an input component for providing navigation control and functionality related to the target to the user (quick functions). The VSS system also includes a connection component that connects the VSS to a computer system of the user and transmits navigation outputs to a computer system (connectivity). The VSS system further includes a processor configured to process navigation outputs from the navigation component (one or more sensors) and the input component. The processor further interprets the VSS system's outputs using a preset or user-configured motion/movement model, which is used to implement in software a movement profile to translate (transform) the motion/movement of the target for viewing via an application configured at the user's computer system.

Multiple embodiments of the VSS system will be described, but a preferred embodiment utilizes an opaque target (slide) of roughly the same dimensions as a typical glass slide. The opaque target is placed on a Virtual Slide Stage (VSS) and one or more sensors of different types detect fine (sub-millimeter or micron) movements. Additionally, the VSS can optionally receive additional quick functions for navigating the target, including allowing for navigation between resolutions, different WSIs, or other types of user controls. The VSS system, coupled with the processing for the various inputs, is then paired/coupled with a user's computer and software configured on the user's computer to navigate the target image.

In a preferred embodiment, the VSS system contains one or more optical sensors (similar to an optical mouse) to detect movement of the target, and a series of buttons to implement quick functions to further control movement/navigation of the target. These buttons are connected to the VSS (either directly or via a cable). In other embodiments, the buttons may be replaced with any other input controls without limitation. A processor within the VSS system translates the input (movement of the target) via a model into a movement profile and transmits the translated input (movement profile) to the user's computer via a USB connection, as shown in FIG. 1.

Figure 1:
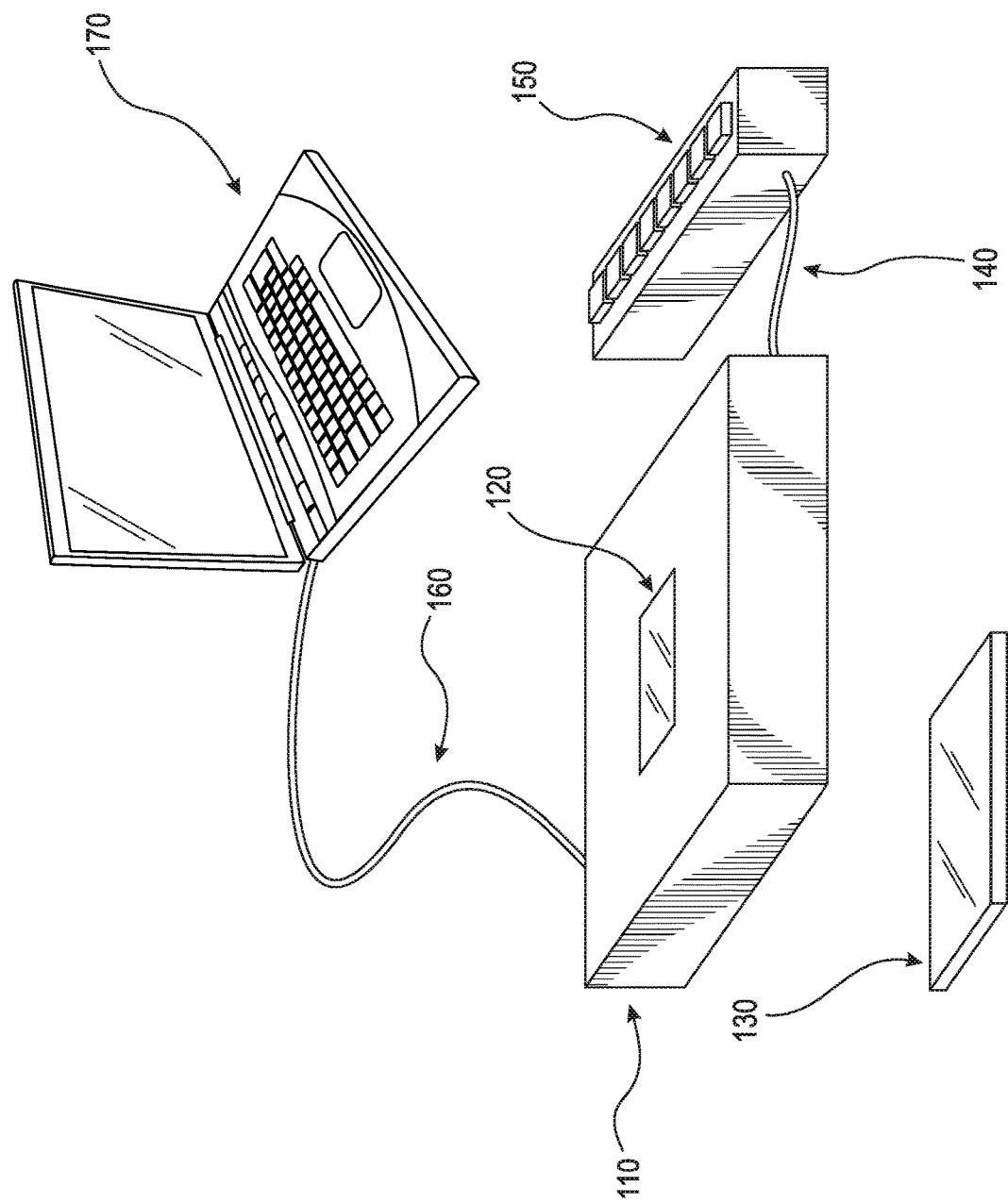
FIG. 1 illustrates one implementation of the VSS method/system, in which a target slide is placed on a flat stage, and the slide's movements are detected by optical sensors.

FIG. 1 illustrates a preferred embodiment of the VSS system and method. The VSS stage (110) contains sensors (120) to detect the relative position and orientation of a "target" or blank slider (130), which can be glass, plastic, or other material, placed on the VSS (110). The target can be any reasonable size, but to best replicate slide movements under a microscope, a 1×3×0.1 inch target (blank slide) can be used to provide familiarity to the user. The stage (110) is a flat surface, on which the target (blank slide) rests, and within which the sensors are mounted. Connected either within the same stage or another component connected via a cable (140), a series of quick functions (150) are implemented. The VSS itself is connected to a user's computer (170) via a connection (160), which may be physical or wireless.

Sensors

Figure 2:
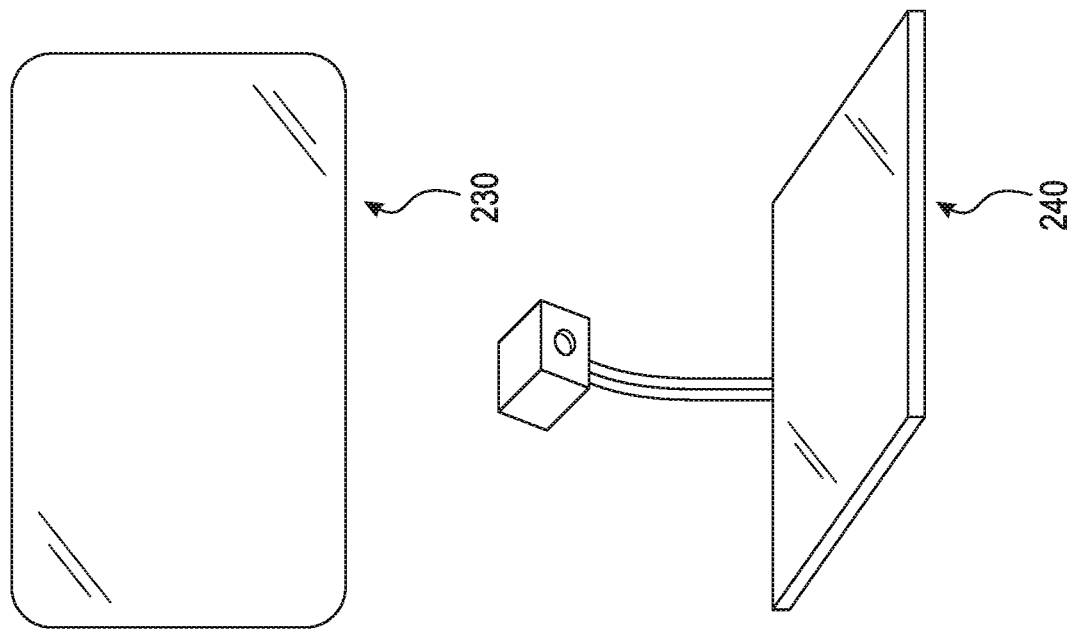
FIG. 2 illustrates different embodiments of sensors in the VSS method/system.
Figure 2:
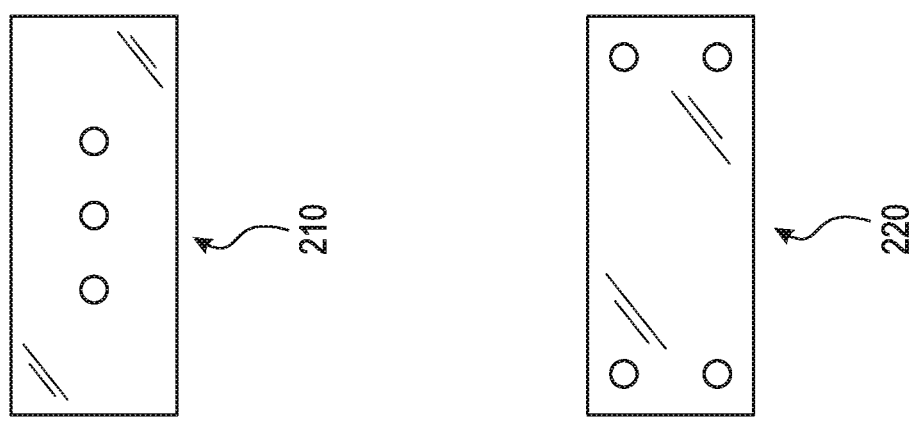

FIG. 2. illustrates different embodiments of the sensors (120) from FIG. 1. In a preferred embodiment, the sensors (210) are optical sensors, each detecting/sensing illumination from one or more light sources or lasers. The sensors are sensitive enough to detect tiny (slight) changes in the position of the blank relative to the stage. In an embodiment with a single optical sensor, the VSS can process the change in the X and Y (horizontal and vertical) position of the target (blank slide), relative to the surface of the VSS. In an embodiment with multiple optical sensors, the VSS can process the change in the X and Y position of the target (blank slide), as well as the rotation of the blank relative to the surface of the VSS (110).

In another embodiment including optical sensors, in place of the combination of light sources (or lasers) and an opaque target, a semi-translucent target slide can be used, allowing ambient light to reach the one or more optical sensors. The use of ambient light allows these embodiments to forego the use of a light source (or laser).

In another embodiment of the sensors, infrared distance sensors can be used in place of optical sensors. The distance sensor are placed to sense the target (blank slide), determining the X/Y position and rotation of the target, thereby replacing the optical sensors. In this embodiment, a thicker target (blank slide) is used. In an embodiment using infrared distance sensors, a pair of sensors mounted in parallel would capture/sense one vertical face of the blank slide. A second pair of parallel sensors would be mounted perpendicular to the first set, capturing/sensing an additional face of the blank slide. This capturing of the vertical faces allows the calculation of the X/Y position of the blank slide, as well as rotation of the blank slide.

In another embodiment of the sensors, sonar (lidar) sensors are used in place of the optical sensors. These sensors use the physical positioning described in the infrared embodiment to calculate X/Y position of the blank slide.

In another embodiment, the VSS (110) may use a highly sensitive touch screen (230) (such as those found on tablets or smartphones) or touch sensor (similar to a touch pad from a laptop) in place of the blank slide and associated sensors. This implementation may determine X and Y position from a user's finger interfacing with the touch screen. Two-finger use would allow the VSS (110) to capture X/Y position and rotation from the user without use of a blank slide.

In another embodiment of the sensors, the VSS (110) may use a camera (240) to capture the relative movement of a target (slide). The target may be an opaque slide that may be marked with specific icons. In one processing method, the VSS camera captures a new image and calculates the movement of the target (opaque slide) by comparing this new image to reference data in memory communicatively coupled to the VSS. This reference data may be one or more video frames recorded from an earlier point in time. In a second processing method, the movement of the target is relative to either the absolute field of view of a camera image, or is relative to some demarcation (e.g., a box drawn on the surface of the VSS) physically marked on the VSS. If the target is marked with icons, those icons' positions in the image may be used for processing in either processing methodology. Any new images taken may also be stored as future reference data in memory communicatively coupled to the VSS.

In another embodiment of the sensors, a set of magnetometers (220) in some configuration are laid out below the surface of the VSS, and the target is magnetized or contains small magnets. The orientation and position of the magnetized target can then be determined by the magnetometers.

Quick Functions

Figure 3:
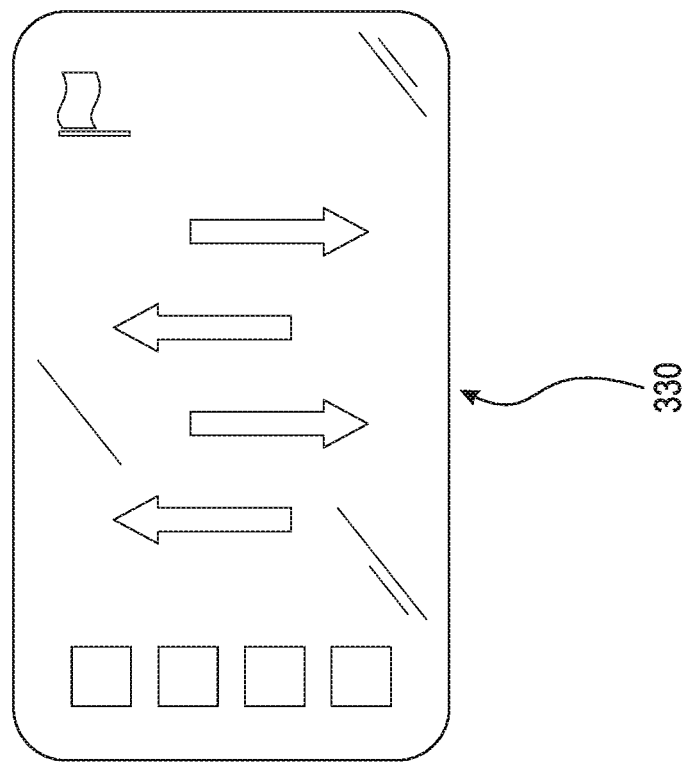
FIG. 3 illustrates different embodiments of quick functions in the VSS method/system.
Figure 3:
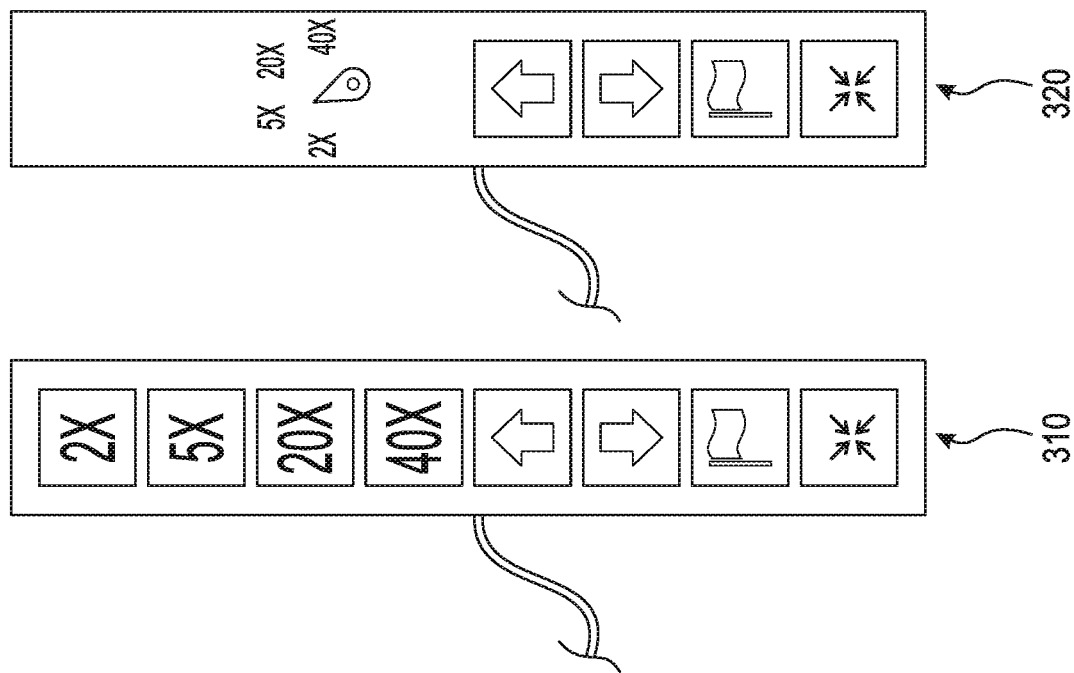

FIG. 3. illustrates a few embodiments of the Quick Functions (150). In the preferred embodiment, the Quick Functions are wholly or partially implemented by a number of keys (310) (for example, 10 keys) to perform some or all of the following functions: a) switch to next slide; b) switch to previous slide; c) flag a slide (i.e., note that the slide is of interest); d) center a slide (in the viewing application on the user's computer system); e-h) change magnifications; i-j) toggling between available focal planes. In one embodiment, magnifications may include 1.0×, 2.5×, 10×, and a maximum (MAX) magnification, usually 20× or 40×, depending on the maximum resolution of the device that captured the image. These keys can be either contained within the structure of the VSS (as shown) or can be on a keypad connected to the VSS via a cable.

In another embodiment, the Quick Functions may be wholly or partially implemented by alternative input devices such as dials, potentiometers, or wheels (320) to control the zoom, either digitally (at preset magnifications) or in a more analog manner (scrolling non-preset amounts).

In another embodiment, one may use voice commands in combination with, or as replacements for all Quick Functions.

In embodiments using a camera or a touch screen (330), such embodiments may include the use of gestures as a replacement for one or more of the Quick Functions.

In another embodiment, the Quick Functions are implemented as a mixture of other embodiment implementations (such as a wheel for magnification and buttons for other Quick Functions).

In another embodiment, there are no Quick Functions implemented.

Digital Processing Environment

Figure 4:
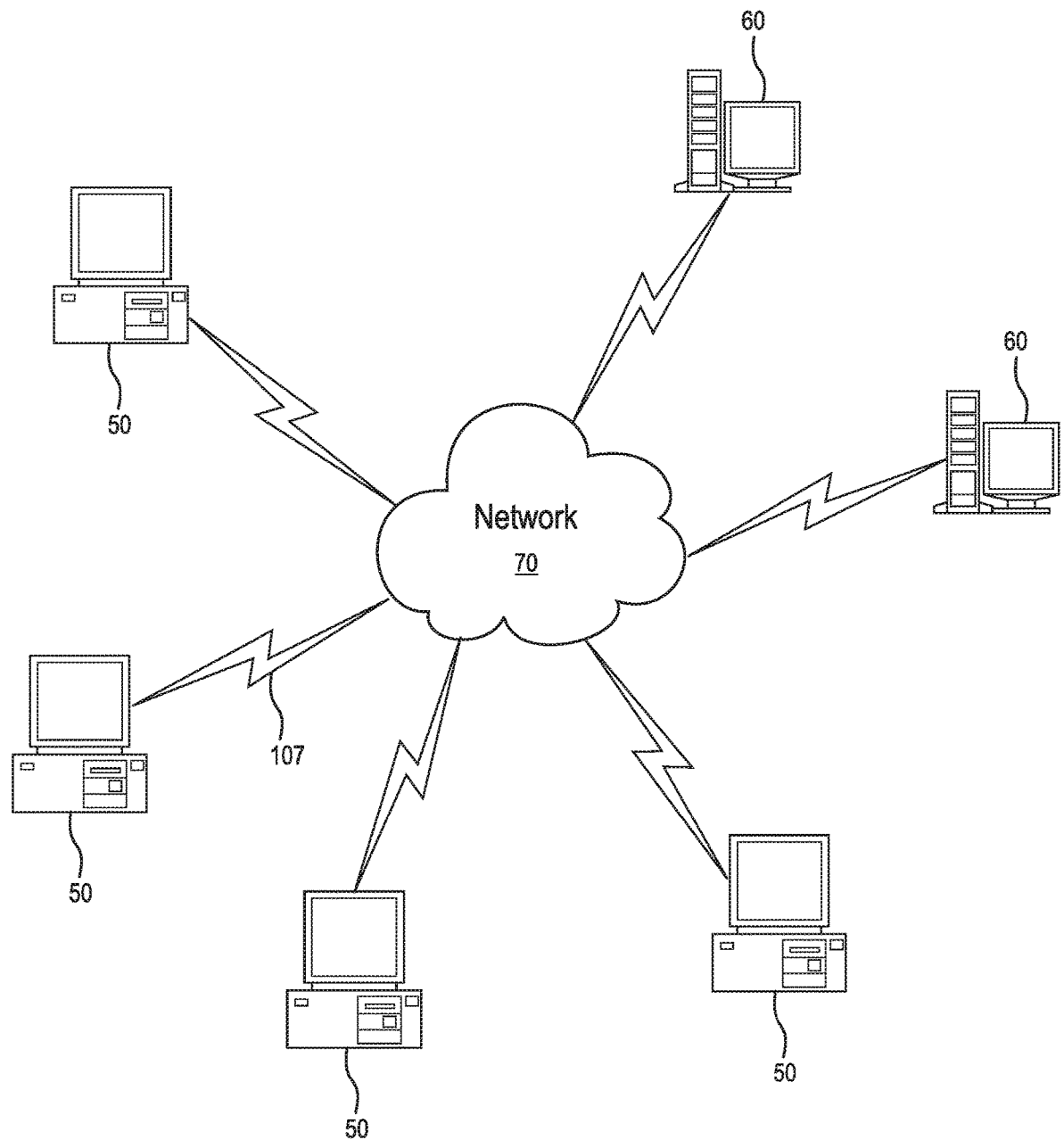
FIG. 4 illustrates is an example digital processing environment in which embodiments of the present invention may be implemented.

FIG. 4 illustrates an example implementation of a slide navigation system according to an embodiment of the invention. The slide navigation system, which enables quickly and efficiently navigating of one or more slides, may be implemented in a software, firmware, or hardware environment. FIG. 4 illustrates one such example digital processing environment in which embodiments of the present invention may be implemented. Client computers/devices 50 and server computers/devices 60 (or a cloud network 70) provide processing, storage, and input/output devices executing application programs and the like. In other embodiments, client computer/devices 50 are locally connected (e.g., via a USB connection) across physical bounds to a processor on the server computers/devices 60 for communicating input to the server computers/devices 60.

Client computer(s)/devices 50 can also be linked through communications network 70 (e.g., via interface 107) to other computing devices, including other client devices/processes 50 and server computer(s) 60. Communications network 70 can be part of a remote access network, a global network (e.g., the Internet), cloud computing servers or service, a worldwide collection of computers, Local area or Wide area networks, and gateways that currently use respective protocols (TCP/IP, Bluetooth, etc.) to communicate with one another. Other electronic device/computer network architectures are suitable.

Client computers/devices 50 may include a Virtual Slide Stage (VSS), as shown in FIG. 1, containing one or more of lasers, sensors, magnetometers, and cameras (as shown FIG. 2) to detect navigation of a target slide (e.g., target slide) placed on an area of the VSS 50. The VSS 50 may also contain Quick Function buttons (as shown in FIG. 3), a wheel, a touch screen, voice controls, or such to allow navigation in relation to the slide. Server computers 60 may be a user computer device, which receives input communication from the VSS 50 (e.g., via a USB, WiFi, Bluetooth, or any other network connector) for presentation on the user computer device 60. For example, embodiments connect the VSS via a USB connection to a local processor on the computers 60 (user's computer). In other embodiments, the VSS may be configured as a "smart device" that connects the VSS via the communications network 70 to the user's computer via a peer connection. The VSS 50 may communicate information regarding the position and orientation of the target to the user computer device 60. For example, the VSS 50 may communicate information related to the Quick Functions, such as moving to previous or next slide, flagging a slide, centering a slide, changing magnification/resolution, switching focal planes, and the like to the user device 60. The server computers may not be separate server computers but part of cloud network.

Figure 5:
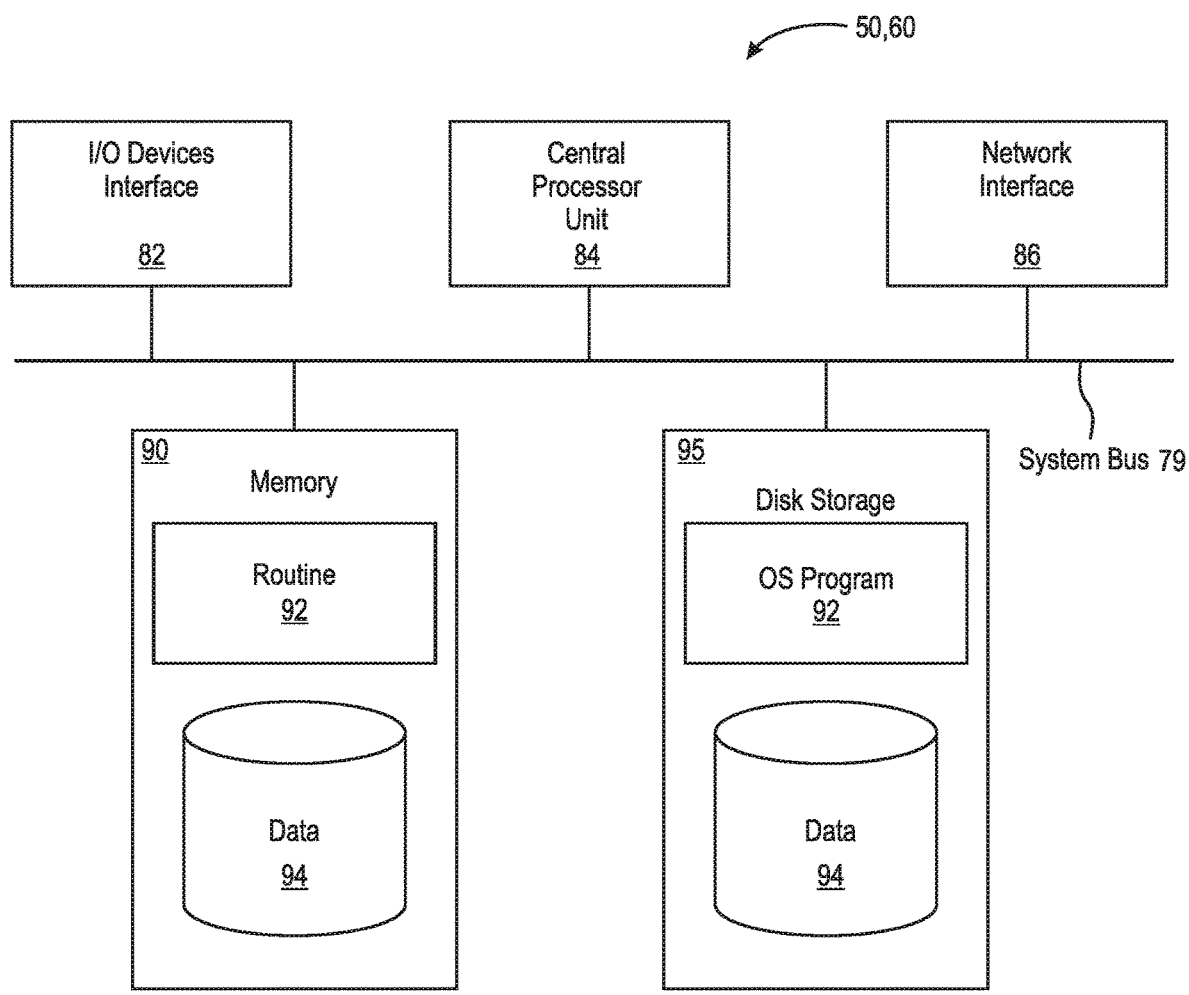
FIG. 5 illustrates is a block diagram of internal structure of a computer/computing node of FIG. 4.

FIG. 5 is a block diagram of the internal structure of a computer/computing node (e.g., client processor/device 50 or server computers 60) in the processing environment of FIG. 4, which may be used to facilitate processing audio, image, video or data signal information. Each computer 50, 60 in FIG. 5 contains system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements.

Attached to system bus 79 is I/O device interface 82 for connecting various input and output devices (e.g., keyboard, mouse, wheels, buttons, touch screens, displays, printers, speakers, voice controls, VSS, Quick Functions, etc.) to the computer 50, 60. Network interface 86 allows the computer to connect to various other devices attached to a network (e.g., network 70 of FIG. 4), such as sensors, cameras, lasers, magnetometers of FIG. 2. Memory 90 provides volatile storage for computer software instructions 92 and data 94 used to implement an embodiment of the present invention (e.g., code detailed above). Software components 92, 94 of the slide navigation system described herein may be configured using any programming language, including any high-level, object-oriented programming language.

In an example mobile implementation, a mobile agent implementation of the invention may be provided. A client-server environment can be used to enable mobile configuration of the capturing of the navigation of slide images. It can use, for example, the XMPP protocol to tether a 50 to VSS 50. The server 60 can then issue commands via the mobile phone on request. The mobile user interface framework to access certain components of the slide navigation system may be based on XHP, Javelin and WURFL. In another example mobile implementation for OS X, iOS, and Android operating systems and their respective APIs, Cocoa and Cocoa Touch may be used to implement the client side components 115 using Objective-C or any other high-level programming language that adds Smalltalk-style messaging to the C programming language.

Disk storage 95 provides non-volatile storage for computer software instructions 92 and data 94 used to implement an embodiment of the slide navigation system. The system may include disk storage accessible to the server computer 60. The server computer (e.g., user computing device) or client computer (e.g., sensors) may store information, such as logs, regarding the navigation of the slide navigation, including position and orientation of one or more slides. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the slide navigation system. Executing instances of respective software components of the slide navigation system, may be implemented as computer program products 92, and can be installed by any suitable software installation procedure, as is well known in the art. In another embodiment, at least a portion of the software instructions may also be downloaded over a cable, communication and/or wireless connection, via for example, a browser SSL session or through an app (whether executed from a mobile or other computing device). In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the routines/program 92 of the slide navigation system.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

In other embodiments, the program product 92 may be implemented as a so called Software as a Service (SaaS), or other installation or communication supporting end-users.
Connectivity In a preferred embodiment for connectivity, the VSS will have a USB connector to connect with the user's computer.

In another embodiment of connectivity, the USB connector that connects the VSS to the user's computer can be an ethernet network connector.

In another embodiment of connectivity, the USB connector that connects the VSS to the user's computer can be replaced by a bluetooth network connection.

In another embodiment of connectivity, the USB connector that connects the VSS to the user's computer can be replaced by a WiFi network connection.
VSS Signal Processing In a preferred embodiment, the processing of the inputs is performed by a processor contained within the VSS itself.

In another embodiment, the VSS may use USB- or network-addressable sensors, allowing a consuming or viewing software application to access data directly from said sensors. In this embodiment, the VSS does not have a local processor. Instead, the processing of the inputs is performed by the processor in the user's computer.

In either processing embodiment, measured inputs by the VSS sensors of the target are transferred into relative movements (relative to the VSS) that are transferred to the user's computer. The user's computer may have a software component installed and running to relay information from the VSS to the consuming or viewing software application, also running on the user's computer. In one embodiment, the software component is a device driver. In another embodiment, the software component is a server component that performs internal networking or data transfer.

In one embodiment, the component will implement Web Sockets, which allows for one or more software components to connect to a Web Socket server, and every connected application (e.g., consuming and viewing applications) of on the user's computer may receive the data packets sent by other connected applications. In this manner, the processor sends both key press and positional information to the connected applications via the server.
Signal Transformation and Modeling The movements of the system corresponding to the target movements can be modeled in multiple ways (and formatted in a movement profile of the target). First, the modeled movements may remain linear to the target slide's movement (independent of magnification). Second, the modeled movements can be scaled geometrically to increase or decrease the responsiveness of the application relative to the movement of the target. Third, a custom movement profile may be created that has user-defined scaling, where the scaling can vary for different ranges of magnification (and thus is neither linear nor geometric).

In the first instance (linear), the modeled movement of the entire range of the WSI image is controlled by the movement of the target (slide) within an approximately 1 inch target region. This means that at low resolutions (e.g., 1×), moving the target ½ inch may translate to about 500 pixels worth of movement on the screen, but at higher resolutions (e.g., 20×), the same movement would correspond to about 10,000 pixels. Regardless of the magnification, the same movement should navigate the user to the same location on the slide.

In the second instance (scaled), the modeled movement of the target slide can be modified to produce finer movements at higher resolutions. The ½ inch movement described above may still be the equivalent of 500 pixels at 1×, but at 20× magnification, the movement could remain at 500 pixels or be scaled by some other arbitrary factor to produce a finer slide navigation (e.g., 1000 pixels).

In an example embodiment, magnification mappings could be configured on a per-user basis. The scaling can be applied as a user or system level configuration in the VSS or in the consuming or viewing application, as can the movement/motion models.
Navigation Analytics Information related to additional context verification test/factors used in determining the performance of navigating a slide at the VSS (e.g., user moving slide or using quick functions to navigate the slide), including information regarding which tests/factors are successfully applied versus those that were processed but were not successfully applied can be used to improve the quality of the VSS. For example, an analytics tool (such as a web analytics tool or BI tool) may produce various metrics such as measures of additional context verification factor/test success based on the combination of other criteria (e.g. variables associated with level of user's movement of the slide), and filter these results by time of the day or time period or location. The analytics tools may further filter results of physically moving a slide by the user versus the user using quick functions to move the slide. The analytics tools may further filter results of switching between slides, versus movement with the slide, changing magnifications, navigating between focal planes, and the like. Such measures can be viewed per test/factor to help improve the VSS and viewing application because the results may be aggregated across a multitude of devices and users.

An analytics tool offers the possibility of associating other quantitative data beside frequency data with a successful test/factor application. For instance, the results of high performance in interactively navigating a target at the VSS could be joined against the metrics derived by an analytics system (such as a web analytics solution or a business intelligence solution).

Furthermore, analytics data for interactive communication within online content for a user can be aggregated per type of user. For example, it could be of interest to know which types of tests/factors are most or least conducive to a high performance in the interactive communication, or on the contrary, applied to a low performance in the interactive communication.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A system for virtually navigating and viewing Whole Slide Images (WSI), the system comprising:
  a virtual slide stage (VSS) having two or more sensors detecting user movement of a target, where the target is a slide that is distinct from a slide used to create the WSI and the target enables a user to virtually navigate the WSI, the target being placed on a surface of the VSS, the user movement detected by the two or more sensors resulting in target movement in the plane of the surface of the VSS, including detecting user rotation of the target;
  the VSS, in communication with a computer processor, computationally transforming the detected user movement including the detected rotation from the two or more sensors into a plurality of user movement profiles of the target, the plurality of the user movement profiles being processed using computational movement models to generate modeled user movement data and rotational computations of the target;

a connector component connecting the VSS to a user device, the connector component configured to transmit the modeled user movement data from the VSS sensors and the user device, the transmitted output representing an approximation of user movement of the target relative to the VSS;

the computer processor, in communication with the VSS, computationally processing the processed modeled user movement data to determine desired movement and rotation of an WSI image, wherein the computationally processing includes processing the detected target rotation in the plane of the surface of the VSS; and the computer processor executing a software component causing the generated processed user movement data to be relayed via a viewing application executing on the user device.

2. The system as in claim 1, wherein the VSS is configured with either: (i) the two or more sensors configured within the surface, or (ii) a camera mounted to the surface.

3. The system as in claim 2, wherein the two or more sensors possess sensitivity levels that enable detecting changes in position of the target relative to the VSS, including detecting slight changes in the position.

4. The system as in claim 3, wherein the computer processor processes the change in horizontal and vertical position of the target relative to the surface of the VSS.

5. The system as in claim 1, wherein the VSS is further coupled to an artificial light source enabling detection of user movement of the target, where the target is an opaque slide, and the two or more sensors are optical sensors that detect the user movement of the opaque slide by sensing light from the artificial light source.

6. The system as in claim 1, wherein the target is a translucent slide, and the two or more sensors are optical sensors that detect user movement of the translucent slide by sensing ambient light.

7. The system as in claim 1, wherein the side of the target is a blank slide, and the two or more sensors include at least one infrared distance sensor that detects user movement of the blank slide by sensing physical positioning of the blank slide.

8. The system as in claim 1, wherein the target is an opaque slide, and the two or more sensors detect user movement of the opaque slide via a camera; and
wherein at least one of coloration and marking are applied to facilitate the camera tracking and distinguishing the opaque slide from the VSS.

9. The system as in claim 8, wherein the camera captures a new image of the target and the computer processor calculates the user movement of the target by comparing the captured new image to reference data stored in computer memory communicatively coupled to the computer processor, where the reference data is a plurality of video frames recorded from an earlier point in time.

10. The system as in claim 8, wherein the camera captures a new image of the target and the computer processor calculates the user movement of the target by comparing the captured new image to reference data stored in computer memory communicatively coupled to the computer processor, where the reference data is at least one of: an absolute field of view of an image from the camera, or is relative to a demarcation physically drawn on a surface of the VSS.

11. The system as in claim 1, wherein the VSS sensors are magnetometers configured below the surface of the VSS, and the target is magnetized, such that an rotational orientation and position are tracked by the magnetometers positioned below surface of the VSS.

12. The system as in claim 1, wherein a touchscreen or touchpad detects the user movement on the surface of the VSS, rather than the target and the two or more sensors.

13. The system as in claim 1, further including:
(a) one or more keys or buttons coupled to an input component that is mounted or otherwise connected to the VSS, the one or more keys or buttons being at least one of physically-enabled or digitally-enabled components,
(b) a dial or potentiometer, and accept at least one of: (i) digital inputs that enable one or more fixed settings, and (ii) analog inputs that enable scrolling between discrete settings, and
(c) at least one of: gestures, camera detection, touchscreen, or touchpad.

14. The system as in claim 1, wherein the processing of the detected user movement is performed by the computer processor either: (i) within the VSS, or (ii) within the user device.

15. The system as in claim 1, wherein the computer processor is configured at the VSS, and the processed user movement data is transferred to the viewing application via at least one of: (i) a native software or library, including a device driver, and (ii) a networking component, including a web server or websockets.

16. The system as in claim 1, further comprising a model component configured to implement a model of movement of the VSS respective to the user movement of the target, the model implemented to either: (i) remain linear to the user movement of the target independent of magnification, (ii) geometrically scale to increase or decrease the responsiveness of the viewing application relative to the user movement; or (iii) be a user-configured, non-linear, and non-geometrically.

17. A method of virtually navigating and viewing Whole Slide Images (WSI), the method comprising:
detecting, by two or more sensors coupled to a virtual slide stage (VSS), user movement of a target placed on a surface of the VSS, the user movement detected by the two or more sensors resulting in target movement in the plane of the surface of the VSS, including detecting rotation of the target;
computationally transforming the detected user movement including the detected rotation from the two or more sensors into a plurality of movement profiles of the target, the plurality of the movement profiles being processed using computational movement models to generate modeled user movement data and rotational computations of the target;
transmitting the modeled user movement data from the VSS sensors; the transmitted output representing an approximation of user movement of the target relative to the VSS;
computationally processing the modeled user movement data to determine desired movement of a WSI image, wherein the processing includes processing the detected target rotation of the WSI image in the plane of the surface of the VSS; and
relaying the generated processed movement data, via a viewing application configured on the user device.

18. A device configured to navigate and view Whole Slide Images (WSI), the device comprising:
- a virtual slide stage (VSS) having two or more sensors detecting user movement of a target placed on a surface of the VSS, the user movement detected by the two or more sensors resulting in target movement in the plane of the surface of the VSS, including detecting rotation of the target;
- an input, coupled to the VSS, providing movement control of the target;
- a communication connection connecting the VSS to a remote user device and transmitting output from the two or more VSS sensors and the input component to the user device, the transmitted output representing user movement of the target relative to the VSS;
- the VSS, in communication with a computer processor, computationally processing the transmitted output into approximated user rotation predictions of the target, the approximated user rotation predictions being transformed into a plurality of the user movement profiles to generate modeled movement data and rotational computations of the target; and
- the computer processor, in communication with the VSS, computationally processing the modeled user movement data and rotational computations of the target to represent desired movement of a WSI image, the computer processor executing software, which causes the generated processed user movement data to be relayed via a viewing software application executing on the user device, wherein the computationally processing includes processing the detected target rotation in the plane of the surface of the VSS.

* * * * *